United States Patent
Krauss et al.

(10) Patent No.: US 8,666,129 B2
(45) Date of Patent: Mar. 4, 2014

(54) CONTRAST INTENSIFICATION OF CT IMAGES BY WAY OF A MULTIBAND FILTER

(75) Inventors: Bernhard Krauss, Burgthann (DE); Rainer Raupach, Heroldsbach (DE)

(73) Assignee: Siemens Aktiengesellschaft, Munich (DE)

(*) Notice: Subject to any disclaimer, the term of this patent is extended or adjusted under 35 U.S.C. 154(b) by 811 days.

(21) Appl. No.: 12/770,825

(22) Filed: Apr. 30, 2010

(65) Prior Publication Data
US 2010/0278411 A1 Nov. 4, 2010

(30) Foreign Application Priority Data
May 4, 2009 (DE) .................. 10 2009 019 840

(51) Int. Cl.
*G06K 9/00* (2006.01)
*G06K 9/62* (2006.01)

(52) U.S. Cl.
USPC .......................................... 382/128; 382/130

(58) Field of Classification Search
USPC .......................................... 382/128; 328/128
See application file for complete search history.

(56) References Cited

U.S. PATENT DOCUMENTS

| | | | |
|---|---|---|---|
| 4,825,297 A | 4/1989 | Fuchsberger et al. | |
| 5,051,902 A | 9/1991 | Hishinuma | |
| 6,956,975 B2 | 10/2005 | Young | |
| 7,804,988 B2 | 9/2010 | Flohr et al. | |
| 2002/0191737 A1* | 12/2002 | Tanigawa | 378/19 |
| 2004/0017888 A1* | 1/2004 | Seppi et al. | 378/57 |
| 2004/0252907 A1 | 12/2004 | Ito | |
| 2007/0147674 A1 | 6/2007 | Gundel | |
| 2009/0161935 A1 | 6/2009 | Bruder et al. | |

FOREIGN PATENT DOCUMENTS

| | | |
|---|---|---|
| CN | 101034473 A | 9/2007 |
| CN | 101097627 A | 1/2008 |
| DE | 3629409 A1 | 3/1988 |
| DE | 102005038940 A1 | 3/2007 |
| DE | 102007061935 A1 | 6/2009 |
| JP | 2005270577 A | 10/2005 |

OTHER PUBLICATIONS

Salvador, Neurophysiological Architecture of Functional Magnetic Resonance Images of Human Brain, 2005, Cereb. Cortex 15 (9): 1332-1342.*
Chinese Office Action dated Sep. 4, 2013 for corresponding Chinese Application No. 201010169283.4.

* cited by examiner

*Primary Examiner* — Tran Nguyen
(74) *Attorney, Agent, or Firm* — Harness, Dickey & Pierce, P.L.C.

(57) ABSTRACT

A method is disclosed for processing an output image of an examination object, with the output image having been reconstructed from measuring data acquired during a relative rotational movement between a radiation source of a computed tomography system and the examination object. An image frequency division of an output image takes place in at least a first and a second image. In at least one embodiment, the first image is changed by way of a first function, with the first function effecting a contrast intensification within the first image, and the changed first image and the second image are merged together.

19 Claims, 8 Drawing Sheets

CONTRAST INTENSIFICATION OF CT IMAGES BY WAY OF A MULTIBAND FILTER

PRIORITY STATEMENT

The present application hereby claims priority under 35 U.S.C. §119 on German patent application number DE 10 2009 019 840.7 filed May 4, 2009, the entire contents of which are hereby incorporated herein by reference.

FIELD

At least one embodiment of the invention generally relates to a method for processing an output image of an examination object, with the output image having been reconstructed from measuring data, which was acquired during a relative rotational movement between a radiation source of a computed tomography system and the examination object.

BACKGROUND

Methods for scanning an examination object using a CT system are generally known. Circular scannings, sequential circular scannings are used here for example with advance or spiral scannings. With these scannings, absorption data relating to the examination object is recorded from different recording angles with the aid of at least one x-ray source and at least one opposite detector and this thus collected absorption data and/or projections are calculated by means of corresponding reconstruction methods to form sectional images through the examination object.

To reconstruct computed tomography images comprising x-ray CT data records of a computed tomography device (CT device), i.e. of the detected projections, a so-called filtered back projection method (FBP) is nowadays used as a standard method. After the data acquisition, a so-called "rebinning" step is implemented, in which the data generated with the beam propagating in the manner of a fan from the source is rearranged such that it exists in a similar form to that obtained when the detector was struck by x-ray beams running in parallel onto said detector. The data is then transformed into the frequency range. A filtering takes place in the filtering range, and the filtered data is then back-transformed. A back-projection onto the individual voxel within the volume of interest then takes place with the aid of the thus rearranged and filtered data.

As diagnostically relevant information is to be taken from CT images for the patients, a high image quality is extremely important. Because the examination object has been exposed to a radiation dose in order to detect the CT projections, this should not have been "purposeless". The quality of a CT image depends in particular on the contrast-to-noise ratio. A high contrast enables limits between different materials/tissue types to be able to be clearly identified. It is endeavored to obtain as good a contrast-to-noise ratio of the CT images as possible with the given radiation dose.

SUMMARY

In at least one embodiment of the invention, a method is disclosed for processing CT images, whereby it should be taken into consideration that a high contrast-to-noise ratio is aspired to. Furthermore, in at least one embodiment a corresponding control and computing unit, a CT-system, a computer program and a computer program product are also to be indicated.

At least one embodiment of the inventive method relates to the processing of an output image of an examination object. This output image was reconstructed from measurement data, which was acquired during a relative rotational movement between a radiation source of a computed tomography system and the examination object. An image frequency division of the output image into at least a first and a second image takes place. The first image is changed by means of a first function, with the first function effecting a contrast increase within the first image. The changed first image and second image are then merged together.

An already reconstructed CT image is therefore firstly available. This may have been determined by way of a reconstruction method which is known per se. This output image is processed as detailed below by way of at least one embodiment of the inventive method.

To this end, an image frequency division takes place at the start. Several images are herewith generated from the one output image. The number of these images amounts to at least two. These several images differ in terms of frequencies and/or frequency spectra of the output image, which they contain. It is possible to achieve a representation of the image in the frequency space from the representation of the same image in the position space, through the implementation of a Fourier transformation. The calculation of the first and second image from the output image can either be implemented in the position space or in the image frequency space.

It is essential that the result of this calculation, i.e. the first and the second image, represents a frequency-related division of the output image. The division can be embodied such that a first part of the image frequencies of the output image is located in the first image and a second part of the image frequencies of the output image is located in the second image, with no overlap existing between the first and second part. To this end, it is alternatively also possible for image frequencies of the output image to exist, which are located both in the first and also in the second part.

With respect to the first image, a modification takes place by way of a first function. The first function effects a contrast increase within the first image. The first function is preferably a non-linear function. The contrast increase can also involve an increase in the noise within the first image.

With respect to the second image, it is possible, but not however necessary, likewise to perform a change. To obtain a result image, the changed first and the, if necessary also changed, second image are merged together again. This merging renders the previously executed image frequency division reversible.

In one development of at least one embodiment of the invention, the first image is a low frequency image and the second image is a high frequency image. This means that the first image contains the low image frequencies of the output image, while the second image contains the higher image frequencies of the output image. An overlap between the image frequencies of the first and second image is herewith possible. The division into the low and high image frequencies is therefore particularly advantageous since, in the case of CT images, only minimal noise is contained in the low image frequency by comparison with the high image frequencies. This can be taken into account in the subsequent change of the first and if necessary also of the second image.

In accordance with one embodiment of the invention, the first function effects a contrast intensification which is restricted to a specific image value range of the first image. An image consists of individual pixels, which are each assigned an image value. The contrast intensification does not take place in respect of all pixels, but only in respect of such pixels, the image values of which fall within the specific image value range. This image value range preferably concerns typical image values for the material which is of particular interest in the output image.

It is advantageous if the first function is applied pixel-by-pixel to the first image. This pixel-by-pixel application means that an individual pixel is used, and its image value is changed by means of the first function. The next pixel is then used etc. This takes place for all pixels in the first image.

According to a development of at least one embodiment of the invention, the first function is a piecemeal linear function with at least one section having an increase of greater than one. This section enables the contrast intensification, since as a result of this type of increase, image values are further removed from one another than was the case in the unchanged first image.

In accordance with a development of at least one embodiment of the invention, the second image is changed by way of a second function, preferably a non-linear function. The second function preferably differs from the first function. This enables the second image to be treated differently to the first image so that the properties of the different image frequencies of the output image can be accounted for in different ways.

It is advantageous if the second function brings about a noise reduction within the second image. This is particularly advantageous if the second image, as a result of the image frequencies of the output image which are contained in the second image contain a large part of the noise of the output image.

The noise reduction by way of the second function can herewith be restricted to an image value range of the second image. This image value range is preferably a region with smaller image values. The noise has a particularly strong effect hereon. The extension of the image value range can be determined as a function of the extent of the noise of the second image. If it contains a lot of noise, a larger image value range is to be subjected to the noise reduction, while a smaller image value range is sufficient with less noise.

The second function is preferably applied to the second image pixel by pixel. This procedure has already been explained in respect of the first image.

In one development of at least one embodiment of the invention, the second function outside the image value range effects a contrast intensification within the second image. The second function therefore comprises at least one image value range, within which a noise reduction takes place, and one or several further image value ranges, within which a contrast intensification takes place. This positive effect of the contrast intensification contributes to the contrast increase in the result image, the contrast intensification having been effected within the first image by the change by means of the first function.

For image frequency division purposes, the output image can be subjected to different filterings, with a first filtering being used to calculate the first image and a second filtering being used to calculate the second image. In one embodiment of the invention, the image frequency division of the output image takes place by means of at least one Gaussian filter. Such a Gaussian filter can be used for the first and/or the second image.

According to one development of at least one embodiment of the invention, the image frequency division of the output image takes place in the first, the second and a third image; the second image is changed by means of a second function and the third image is changed by means of a third function, with the second and third function differing from one another. This procedure can also be applied to a larger number of images.

The use of different functions to change the second and third image enables the properties of the different frequency components of the output image to be detailed suitably.

The result image can correspond to a sum of the changed first image and the possibly changed second image. This summation takes place pixel by pixel. If the image frequency division takes place in more than two images, this further image or these further images, if necessary after a change, will also be added to the changed first and the if necessary changed second image, in order to obtain the result image. The result image is the result of the effected processing of the output image and represents an improvement in the output image in respect of the contrast. Alternatively to the explained summation, the result image can also correspond to a total of the changed first image, the, if necessary, changed second image and the output image. In this case, the changed first and the, if necessary also changed, second image can be seen as differential images to the output image.

In one development of at least one embodiment of the invention, a non-linear function is applied to the output image for the first image prior to implementing the image frequency division. This also does not necessarily apply in respect of the second image, i.e. to determine the second image the original output image can be used without applying the non-linear function. The non-linear function preferably brings about a limitation of relatively large image values.

The inventive control and computing unit of at least one embodiment is used to process an output image of an examination object, with the output image having been reconstructed from measuring data, which was acquired during a rotational movement of a radiation source of a computed tomography system about the examination object. It includes a program memory for storing program codes, with, if necessary inter alia, a program code being present herein which is suited to executing a method of the afore-cited type. It can also include program codes which enable the reconstruction of the output image from the measuring data. At least one embodiment of the inventive CT system includes such a control and computing unit. It can also contain other components which are needed to acquire measuring data.

At least one embodiment of the inventive computer program has program code segments, which are suited to implementing the method of the afore-cited type, if the computer program is executed on a computer.

At least one embodiment of the inventive computer program product includes program code segments stored on a machine-readable data carrier, which are suited to implementing the method of the afore-cited type if the computer program is executed on a computer.

BRIEF DESCRIPTION OF THE DRAWINGS

The invention is described in more detail below with reference to an example embodiment, in which.

DETAILED DESCRIPTION OF THE EXAMPLE EMBODIMENTS

Figure 1:
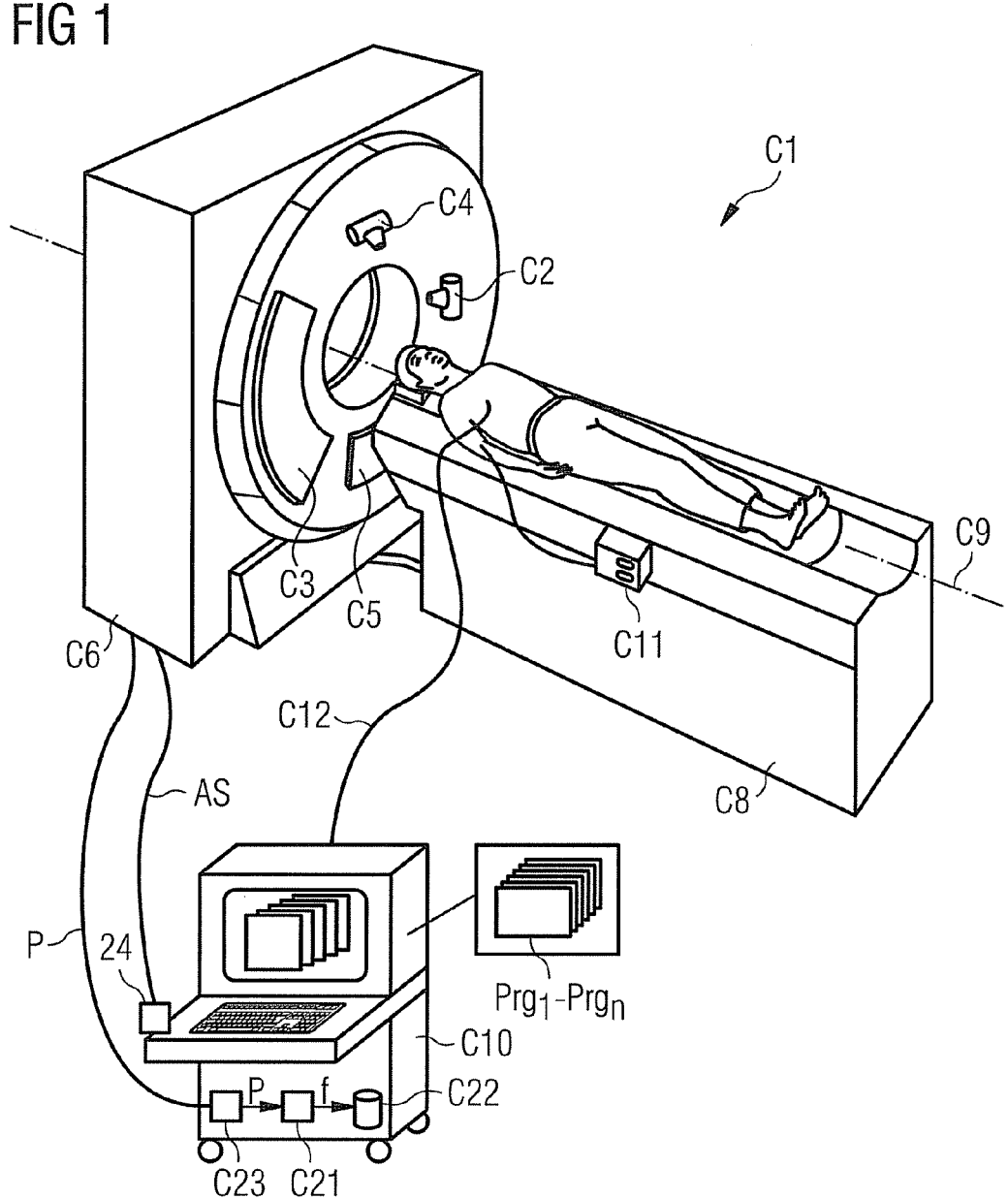
FIG. 1: shows a first schematic representation of an example embodiment of a computed tomography system with an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 firstly shows a schematic representation of a first computed tomography system C1 with an image reconstruction facility C21. A closed gantry (not shown here) is located in the gantry housing C6, on which gantry is arranged a first x-ray tube C2 with an opposite detector C3. In the CT system (shown here), a second x-ray tube C4 is optionally arranged with an opposite detector C5, so that a higher time resolution can be achieved by the emitter/detector combination also available, or "dual energy" examinations can also be implemented during the use of different x-ray energy spectra in the emitter/detector systems.

The CT system C1 also has a patient couch C8, on which a patient can be moved into the measuring field during the examination along a system axis C9, also known as z-axis, with it being possible for the scanning itself to take place exclusively in the examination region of interest both as a purely circular scan without advancing the patient. In this way, the x-ray source C2 and/or C4 rotates in each instance about the patient. The detector C3 and/or C5 proceeds in parallel here relative to the x-ray source C2 and/or C4 in order to acquire projection measuring data which is then used to reconstruct sectional images. Alternatively to a sequential scan, in which the patient is moved step-by-step between the individual scans through the examination field, it is naturally also possible to provide a spiral scan, in which the patient is continuously moved along the system axis C9 through the examination field between the x-ray tube C2 and/or C4 and detector C3 and/or C5 during the circumferential scanning process. The movement of the patient along the axis C9 and the simultaneous circulation of the x-ray source C2 and/or C4 produces a helical path in the case of a spiral scan for the x-ray source C2 and/or C4 relative to the patient during the measurement.

The CT system 10 is controlled by a control and computing unit C10 with computer program codes $Prg_1$ to $Prg_n$ present in a storage device. Acquisition control signals AS can be transmitted by the control and computing unit C10 via a control interface 24 in order to control the CT-system C1 in accordance with specific measurement protocols.

The projection measuring data p acquired by the detector C3 and/or C5 (also referred to below as raw data) is transmitted to the control and computing unit C10 via a raw data interface C23. This raw data p is, if necessary after a suitable preprocessing, further processed in an image reconstruction component C21. The image reconstruction component C21 is realized in this example embodiment in the control and computing unit C10 in the form of software on a processor, e.g. in the form of one or several of the computer program codes $Prg_1$ to $Prg_n$. Besides the image reconstruction, the component C21 can also perform a subsequent processing of the reconstructed images. The result images f from the image reconstruction component C21 are then stored in a storage device C22 of the control and computing unit C10 and/or displayed in a conventional manner on the monitor of the control and computing unit C10. The result images can also be fed, via an interface (not shown in FIG. 1) into a network connected to the computed tomography system C1, for instance a radiological information system (RIS) and stored in a mass storage device which is accessible there or displayed as images.

In addition, the control and computing unit C10 can also execute the function of an ECG, with a line C12 for dissipating the ECG potentials between the patient and control and computing unit C10 being used. The CT system C1 shown in FIG. 1 also has a contrast agent injector C11, by way of which additional contrast agent can be injected into the blood circulation of the patient so that the vessels of the patient, in particular the heart chambers of the beating heart, can be better displayed. Furthermore, there is herewith also the possibility of implementing perfusion measurements, to which the proposed method is likewise suited.

Figure 2:
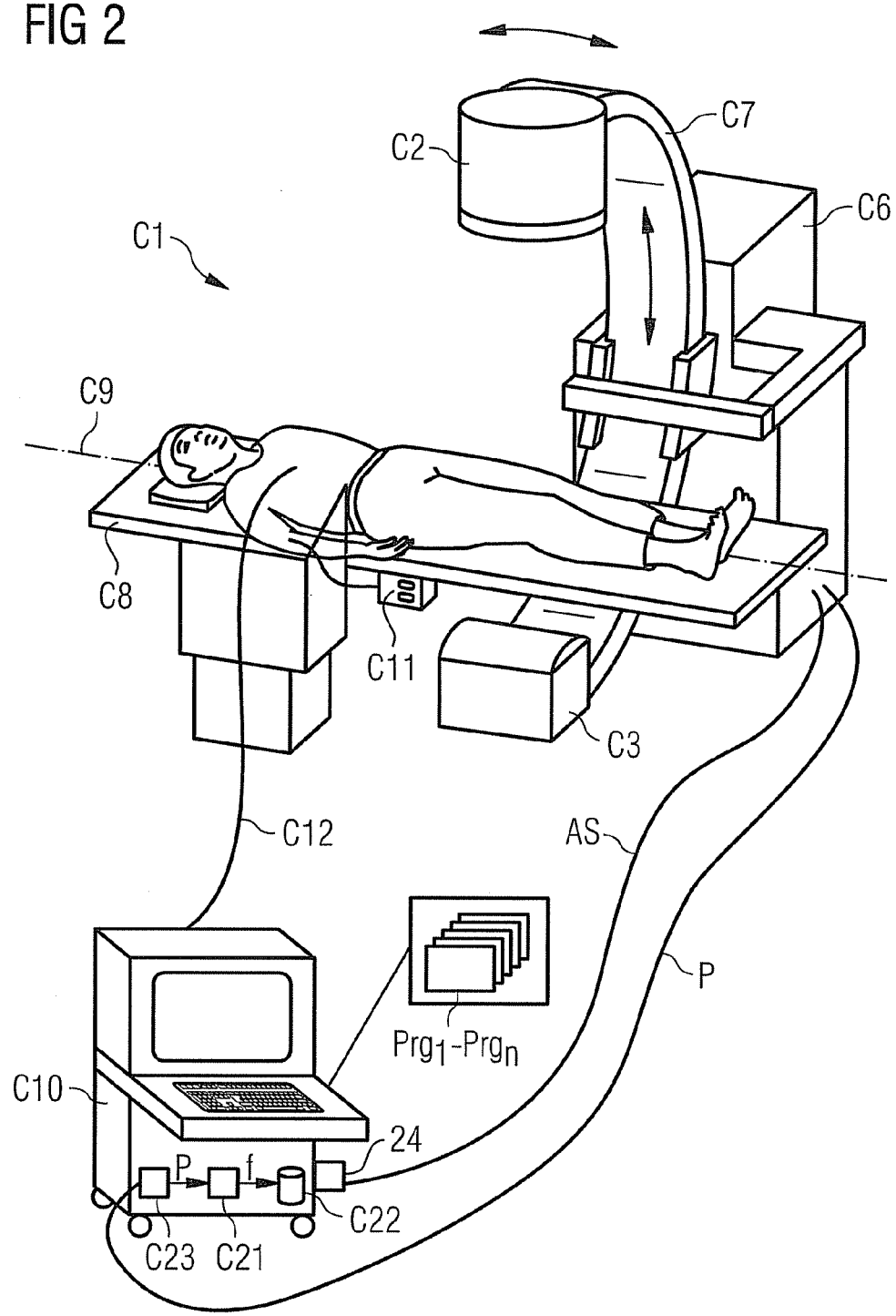
FIG. 2: shows a second schematic representation of an example embodiment of a computed tomography system with an image reconstruction component.

FIG. 2 shows a C-arm system, in which, contrary to the CT system in FIG. 1, the housing C6 supports the C-arm C7, to which the x-ray tube C2 on the one hand and the opposite detector C3 on the other hand are fastened. The C-arc C7 is likewise pivoted about a system axis C9 for a scanning, so that a scanning can take place from a plurality of scanning angles and corresponding projection data p can be determined from a plurality of projection angles. The C-arc system C1 in FIG. 2, similarly to the CT system from FIG. 1, likewise has a control and computing unit C10 of the type described in FIG. 1.

An embodiment of the invention can be used in both systems shown in FIGS. 1 and 2. It can basically also be used for other CT systems, e.g. for CT systems with a detector forming a complete ring.

It is assumed below that an image of the examination object was determined with the control and computing unit C10, referred to below as output image I. Image reconstruction methods which are known per se can be used here. The application is described in an individual axial image in order to describe the procedure. Embodiments of the invention are however not restricted to two-dimensional images, but can instead also be applied to 3D images. This can takes place by a volume data record being interpreted as a stack of axial images, or by the use of 3D instead of 2D band filters described below. The output image is then, as described in more detail below, further processed by the control and computing unit C10 in order to obtain an improved result image.

The quality of a CT image depends, in addition to its intensity, on its contrast-to-noise ratio (CNR). An increase in the CNR with an identical radiation dose for the examination object and/or a reduction in the dose with an identical diagnostic value is desirable.

Increasing the applied dose during the absorption reduces the noise in the image data. An improvement in the CNR would therefore be possible by increasing the x-ray intensity, but the patient dose is however also increased in this way, which is however generally unwelcome.

A further principle possibility of increasing the CNR is the use of iodine-containing contrast agents. This acts such that the contrast of the tissue receiving the contrast agent is strengthened compared with the surrounding tissue. The reason for this is that a stronger absorption takes place with lower x-ray energies as a result of the contrast agent. This effect is stronger than the overall increase in absorption of the x-rays, which is produced by a reduction in the energy of the x-rays. With the use of iodine-containing contrast agents, the dose can therefore be lowered by reducing the energy of the x-rays. There is however the limitation in practice that the available quantum flows with low x-ray voltages are not sufficient for more corpulent patients in order to achieve a CNR which compares to that of higher voltages.

The quantum energy reduction approach in the case of native CT recordings, therefore in the case of recordings without the use of contrast agent, is generally not successful, because the tissue contrasts, compared with iodine, are only slightly energy-dependent relative to the soft tissue.

Below shows how the information in the CT image which relates to the achievable CNR can be used better by using a multiband filter.

The output image I is firstly broken down into frequency bands by band filter $F_k$ (k=1, ..., N), $$I^{(k)} = F_k * I. \qquad (1)$$

Without restriction, $I^{(1)}$ is the band with the lowest frequencies and for increasing frequencies, k represents the increasing frequencies.

In equation (1), I is the image in the two-dimensional position space, i.e. for each point in the position space I indicates an HU value. In the position space, the band filter $F_k$ is applied to the image I by means of a convolution $I^{(k)} = F_k * I$.

Observation in the position space is equivalent to observation in the frequency space. Frequency space representation of the image is achieved by the position space image I being transformed in the frequency space using Fourier transformation. Since the two observations are equivalent, switching between the two is carried out hereafter for improved clarity so as to indicate the respective process in the domain which is to be more effectively clarified.

Figure 3:
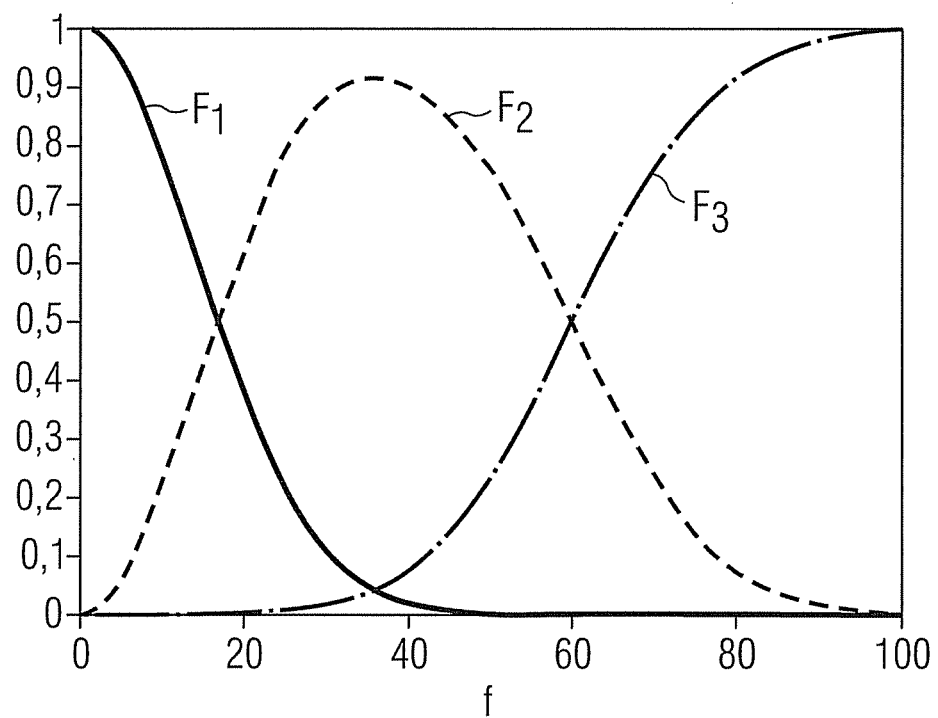
FIG. 3: shows three band filters.

If the filtering specified in equation (1) is executed in the frequency space, a multiplication is generated instead of the convolution. The band filters $F_k$ are frequency-dependent functions in the frequency domain; they can also be obtained by a Fourier transformation from the representation of the band filter $F_k$ in the local space. FIG. 3 shows frequency filters $F_1$, $F_2$ and $F_3$ for the case N=3 in a single frequency dimension. The y-axis indicates a dimension-less weighting and/or transmission factor, while the x-axis represents the frequency f in random units.

One example of the mathematical realization of functions of this type is that the filter $F_1$ is realized for the first frequency band by means of a Gaussian function. $F_1$ therefore represents a low pass filter. The filter $F_k$ for the bands with higher frequencies can therefore be constructed successively ascending in the frequency such that for the filter $F_k$ belonging to band k, the complement to one of the total of the already calculated filter functions $F_1, \ldots, F_{k-1}$, is used multiplied with a further Gaussian function. The band of the highest frequency is finally the complement to one of the total of all filters calculated beforehand.

The frequency space, as with the position space, is two-dimensional. To facilitate the representation, FIG. 3 shows a radial section of the frequency representation of the filter. As this is an isotropic filter, a symmetrical extension of the representation of FIG. 3 has to take place for a two-dimensional representation of the filter.

The filters advantageously fulfill the condition $$\sum_{k=1}^{N} F_k \equiv 1.$$

In the frequency space. By adding the components, the output image i.e.

$$\sum_{k=1}^{N} I^{(k)} \equiv I$$

results again.

By applying the three filter functions according to FIG. 3 to the output image according to equation (1), three images $I^{(k)}$ are thus obtained. The low-frequency image $I^{(1)}$ is herewith particularly important. Since the filter was advantageously determined for the first low-frequency determined such that its amplitude at the zero frequency is equal to one, as shown in FIG. 3, the whole equivalent value part of the image I is already contained in $I^{(1)}$. The pixel values of $I^{(1)}$ accordingly represent the weighted average values of the surroundings of the corresponding pixel of I. All other band images for k>1 are consequently zero-mean.

The images $I^{(k)}$ are now processed separately from one another, with the aim of increasing the CNR of the result image in respect of the output image I. The band parts, i.e. the images $I^{(k)}$, are herewith initially transformed pixel-by-pixel with the aid of functions $G_k$, $$\tilde{I}^{(k)} = G_k(I^{(k)}). \quad (2)$$

Figure 4A:
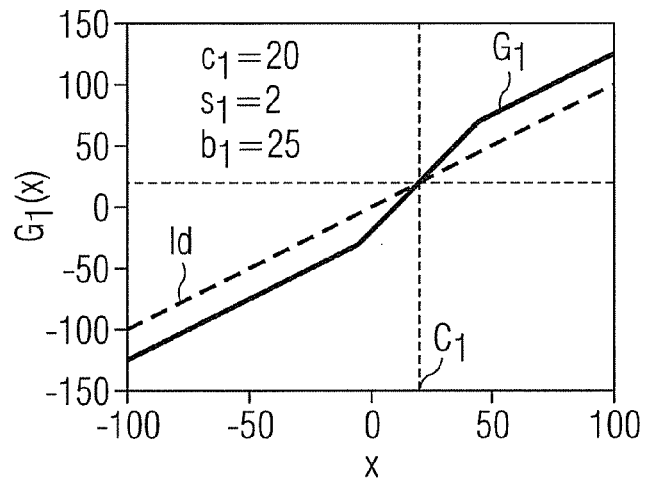
FIG. 4: shows three non-linear functions for distorting low-frequency CT images.
Figure 4B:
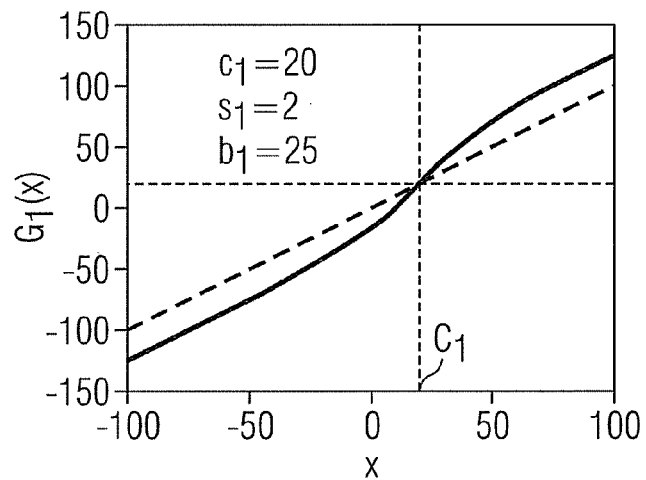
Figure 4C:
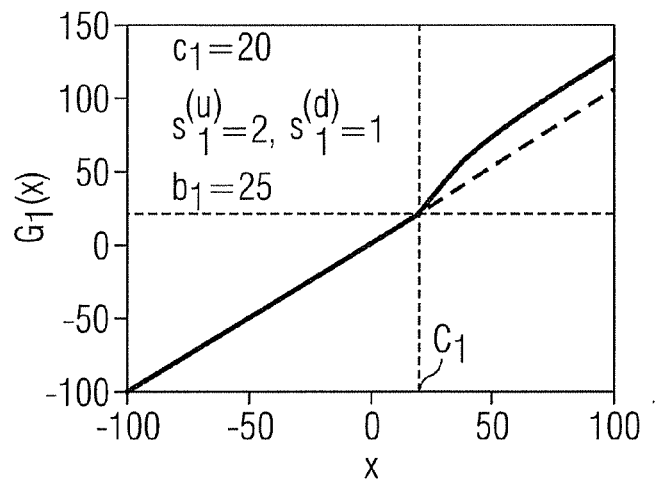

The observation of the first band, in other words the $I^{(1)}$ takes place first. The function $G_1$ used for transformation purposes is shown in FIG. 4. This is the local domain in this Figure. Three alternative possibilities of realizing $G_1$ are shown in FIGS. 4A, 4B and 4C. The initial value x is plotted on the x-coordinate. The respective CT value is in this case in HU units. The result of the transformation is plotted on the y-axis, in other words $G_1(x)$.

In accordance with FIG. 4A, $G_1(x)$ is a piece by piece linear function:

$$G_1(x) = \begin{cases} x + b_1 & \text{für } x > c_1 + b_1/(s_1-1) \\ c_1 + s_1 \cdot (x - c_1) & \text{für } c_1 - b_1/(s_1-1) \leq x \leq c_1 + b_1/(s_1-1) \\ x - b_1 & \text{für } x < c_1 - b_1/(s_1-1). \end{cases} \quad (3)$$

The parameters selected for the representation in FIG. 4A are specified in the Figure.

The application of the function $G_1(x)$ takes place pixel-by-pixel as mentioned, i.e. for each pixel, the value x is replaced by the value $G_1(x)$.

The function $G_1(x)$ works as follows:

The contrast is increased by the factor $s_1 > 1$ by an x-ray value $c_1$. $c_1$ is selected such that it is a value which has the region of interest of the examination object, within which the contrast is to be increased. If a cranium scan is processed for instance, it is advantageous to select $c_1$ as the average value between the HU values of the gray and white brain matter. FIG. 4A has assumed the value 20 for $c_1$. This value is marked on the x-axis by the dashed vertical line.

The identity line Id is also shown in FIG. 4A. These values would result if $G_1(x) = x$.

It can be seen that in terms of value $c_1$, the increase of $G_1(x)$ is greater than that of the identity line Id $c_1$. The increase in $G_1(x)$ in this region is identical to $s_1$, and since $s_1$ has the value 2 in FIG. 4A, the function $G_1(x)$ increases by the value Wert $c_1$ to twice as much as the identity line Id. This means that the distances between adjacent x-values are increased by applying the function $G_1(x)$ in the region about the value $c_1$, in other words a spreading takes place. Larger differences between x-values are therefore effected in this region compared with image $I^{(1)}$, thereby corresponding to a contrast increase.

The maximum absolute change in the pixel values is $b_1$. This corresponds to the distance between the function $G_1(x)$ and the identity line Id with large and small x values.

Instead of the functions shown in equation (3), continuously differenciable functions like for instance $$G_1(x) = x + \frac{(s_1 - 1) \cdot (x - c_1)}{\sqrt{1 + \left(\frac{s_1 - 1}{b_1}\right)^2 (x - c_1)^2}}. \quad (4)$$

can also be used. A function of this type is shown in FIG. 4B, with the parameters $c_1$, $s_1$ and $b_1$ having been selected as in FIG. 4A.

If the contrast is only to be intensified in one direction, the branches for $x \ll c_1$ und $x \gg c_1$ can be selected differently. To this end, the following function can be used:

$$G_1(x) = x + \begin{cases} \dfrac{(s_1^{(u)} - 1) \cdot (x - c_1)}{\sqrt{1 + \left(\frac{s_1^{(u)} - 1}{b_1^{(u)}}\right)^2 (x - c_1)^2}} & \text{für } x \geq c_1 \\ \dfrac{(s_1^{(d)} - 1) \cdot (x - c_1)}{\sqrt{1 + \left(\frac{s_1^{(d)} - 1}{b_1^{(d)}}\right)^2 (x - c_1)^2}} & \text{für } x < c_1. \end{cases} \quad (5)$$

A complete integrity of the contrast below $c_1$ is thus possible for instance, i.e. a contrast intensification takes place exclusively for the x-values above $c_1$. This procedure is then desirable for instance if the x-values below $c_1$ are needed for a specific analysis and are therefore not to be changed. One example of this is quantitative measurements such as the determination of the fat content of the liver.

A non-symmetrical function of this type is shown in FIG. 4C, with the parameters $c_1$, $s_1$ and $b_1$ having been selected as in FIGS. 4A and 4B.

The function $G_1(x)$ according to equations (3), (4) and (5) is used to modify the image $I^{(1)}$ of the lowest frequency band. An increase in the contrast, as described in FIGS. 4A to 4C, must also involve increasing the noise. According to one particular property of CT images, less noise is contained in the lower image frequencies. The contrast increase within the low frequency image $I^{(1)}$ in the result image therefore results in a relatively significant lower change in the noise and thus in an increased CNR. As a result of the transmitted average value, the image $I^{(1)}$ contributes to the essential contrast information of flat structures. The weak noise increase in the image $I^{(1)}$ can be compensated by the measures in the other bands, as is described below.

The other two frequency images are now observed. It is easily assumed herefrom that the same transformation is performed for the two images $I^{(2)}$ and $I^{(3)}$.

The noise in the frequency bands k>1 is $\sigma_k$. (This variable can be calculated by a homogenous surface being selected in the respective image and determining the standard deviation of the pixel values within the surface). It can be assumed herefrom that structures with sufficiently high CNR in the observed frequency band have amplitudes which are larger than $\sigma_k$. It can therefore be assumed that changes between adjacent image values, which are smaller than $\sigma_k$, are only perceived as noise. Contrastingly, such distances between adjacent image values, which are greater than $\sigma_k$, are considered as a structure. This is to be used by flattening taking place in the region of small values, which are readily exposed to noise and by the structure information being intensified in the region of large values.

The function $$G_k(x) = \left(1 + (s_k - 1)\frac{1 - \frac{|x|}{c_k}}{\sqrt{1 + \left(\frac{s_k - 1}{b_k c_k}\right)^2 |x|^4}}\right) \cdot x \quad (6)$$

is used for transformation purposes.

Figure 5:
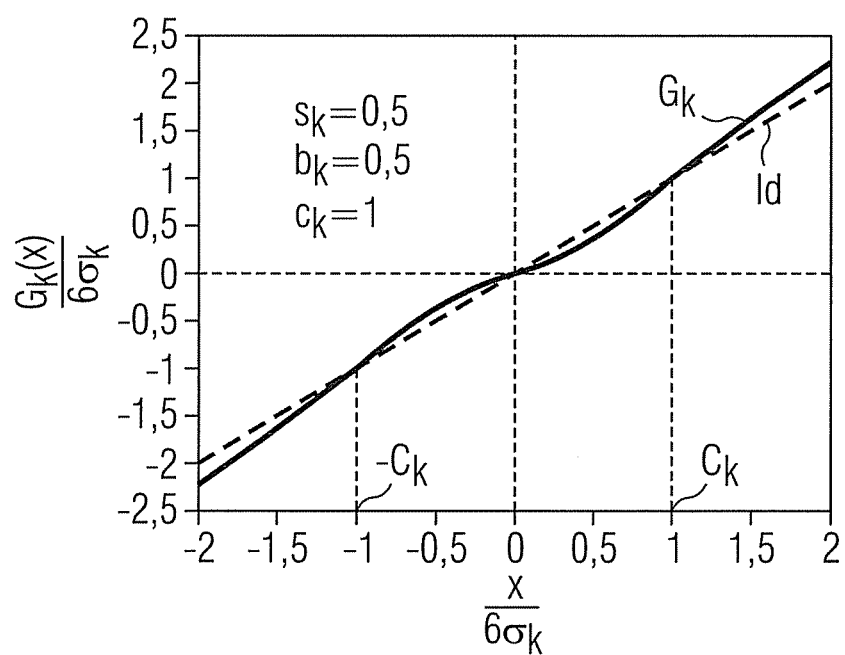
FIG. 5: shows a non-linear function for distorting high-frequency CT images.

A function of this type is shown in FIG. 5 for the parameters $s_k=0.5$, $b_k=0.5$ and $c_k=1$. The output CT values x are plotted here on the x-coordinates scaled with the 6-times of $\sigma_k$, and the transformed values $G_k(x)$, also scaled with 6 times $\sigma_k$ are plotted on the y-axis. The identity line Id is also plotted.

In the region of small x values, the function $G_k(x)$ has a smaller increase than the identity line Id. This increase corresponds to $s_k$, and, with the curve in FIG. 5, is thus half as large as that of identity line Id. This means that small x-values and the distance between them are still further reduced in size. This small transmission amplitude $s_k$ for small signals corresponds to a noise reduction. Basically $s_k<1$ is to be set in order to achieve a noise reduction.

$c_k$ is the equivalent value point. For x-values which are larger than $c_k$, the function $G_k(x)$ increases more significantly than the identity line Id. The large amplitudes are therefore increased further. This effects an increase in the steepness of edges. The equivalent value point can be selected in a suitable fashion compared with the noise part in the band, in other words e.g. $c_k \approx 6\sigma_k$. This is based on the idea that the probability that a structure is contained in the image, the CT values of which differ from the ambient by less than $c_k \approx 6\sigma_k$, is only very minimal. Accordingly $c_k$ in the example in FIG. 5 was selected to be identical to 1, which, on the basis of the scaling of the axes, means that a value increase according to amount takes place for x-values which are greater than or less than 6-times the noise $\sigma_k$.

The parameter $b_k$ determines the maximum increase in the band parts in the case of x-values clearly above the noise.

The described transformations are applied to the individual images, so that the changed images $\tilde{I}^{(k)}$ are then present. For the low frequency image $I^{(1)}$, a different type of transformation is implemented with the function $G_1(x)$ than for the other images $I^{(k)}$ with k>1. It is herewith possible for the same function $G_k(x)$ to be used for all high frequency images $I^{(k)}$ with k>1. Different functions $G_k(x)$ can however also be used from image to image. These can either differ from one another by the selection of the function parameters, or by the functions themselves.

The distorted band parts $\tilde{I}^{(k)}$ are then recombined to form a complete image, the result image $\tilde{I}$:

$$\tilde{I} = \sum_{k=1}^{N} \tilde{I}^{(k)}. \quad (7)$$

Figure 6A:
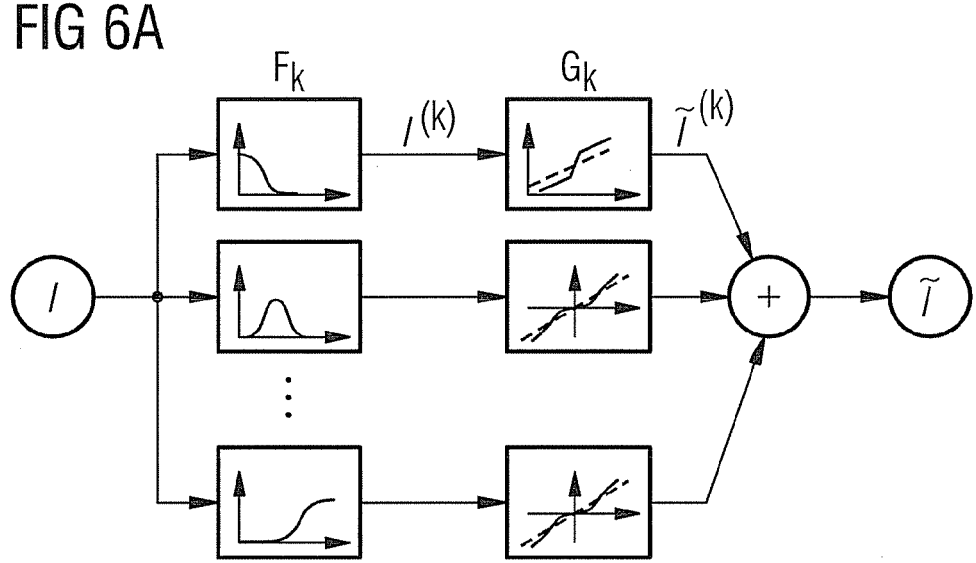
FIG. 6: shows three schematic diagrams for illustrating the sequence of the method.

FIG. 6A shows a schematic representation of the described method: based on the output image I, several band filters $F_k$ are applied to the output image I, so that several images $I^{(k)}$ exist, which represent different frequency ranges of the output image I. A branch in FIG. 6A belongs to the treatment of each band region. The case of dividing into three images $I^{(k)}$ was described by way of example; a division into only two images or into a larger number of images is however also possible.

Each image $I^{(k)}$ is now distorted by using a function $G_k$. This modification takes place pixel by pixel, i.e. for each pixel, the respective Ct value x is used in order to determine a modified CT value by using $G_k(x)$. Changed images $\tilde{I}^{(k)}$ result herefrom. The changed images are then added pixel-by-pixel in order to obtain the result image $\tilde{I}$.

The described method is based on a contrast division with the low local frequencies with the aid of non-linear transformations of the pixel values. In the high frequency bands, which contain a large part of the noise, a non-linear transformation is used in order to reduce the noise and at the same time to further increase the intensity at edges with a very high contrast. An image with contrast-dependent intensity is generated in this way.

Figure 7A:
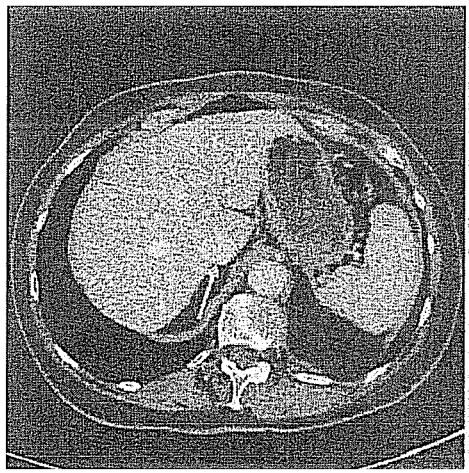
FIG. 7: shows two CT sectional images of a liver.
Figure 7B:
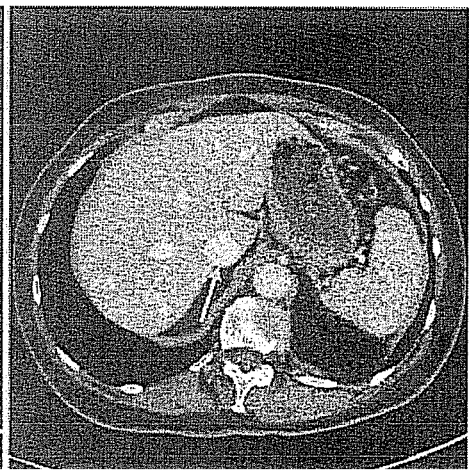

To demonstrate the advantages of the method, a CTA (CT angiography) of the liver is observed in FIG. 7. The aim is a contrast intensification of that tissue which has absorbed the contrast agent. FIG. 7A shows the original image I, and FIG. 7B shows the result image $\tilde{I}$ after implementing the described method.

Two complementary bands were processed, a division of the original image I into two images $I^{(1)}$ and $I^{(2)}$ therefore took place. The low frequency band $I^{(1)}$ was realized by a Gaussian filter with $\sigma=1.1$ LP/cm (line pairs per centimeter). The parameters used are $F_1$: $s_1^{(u)}=2$, $s_1^{(d)}=1$, $b_1=50$, $c_1=110$ for the band filter, and $F_2$: $s_2=0.75$, $b_2=20$, $c_2=180$ for the band filter.

The CT value of the liver tissue without contrast agent is approximately 110 HU, according to parameter $c_1$. The maximum contrast increase is 50 HU, corresponding to parameter $b_1$. Selecting $s_2=0.75$ reduces the noise at small values by approximately ¼. The noise within the high frequency image $I^{(2)}$ amounts to approximately 20 HU.

An improvement in the CNR by factor 1.92 is achieved computationally for the region marked with the arrow, with the contrast with the surrounding tissue being increased by 66% and the noise simultaneously being reduced by 13%.

The method according to FIG. 6A can alternatively be formulated such that differential amounts are calculated for each frequency band instead of modified band parts $\tilde{I}^{(k)}$:

$$\Delta I^{(k)} = G'_k(I^{(k)}), \quad (8)$$

so that $$\tilde{I} = I + \sum_{k=1}^{N} \Delta I^{(k)}. \quad (9)$$

The result which is the same as the original procedure is achieved if $$G'_k(x) = G_k(x) - x. \quad (10)$$

Computing time can be saved in this way, if modifications are not to be carried out in all bands. This procedure is shown in FIG. 6B.

Figure 6B:
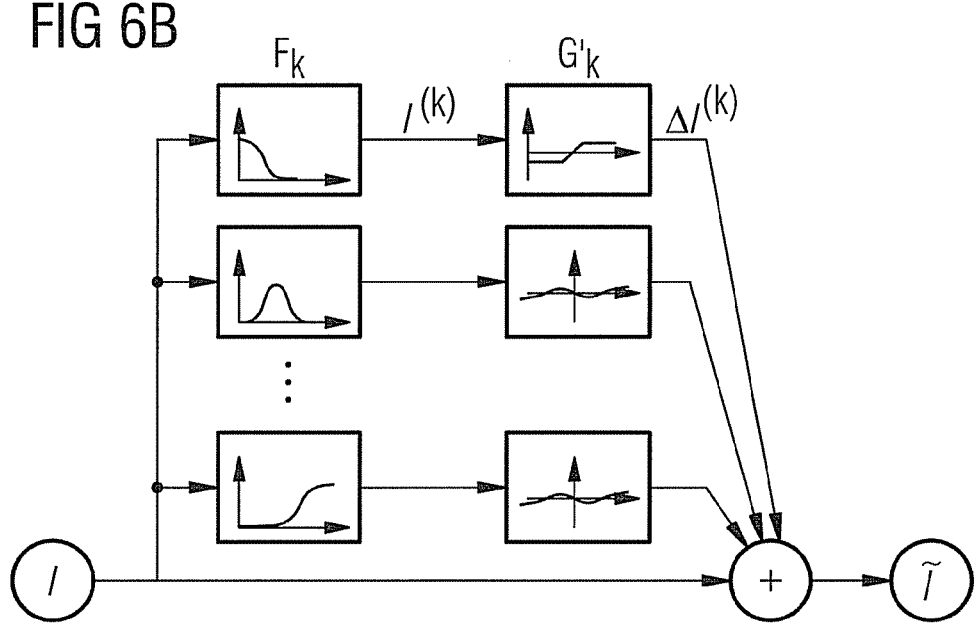
Figure 6C:
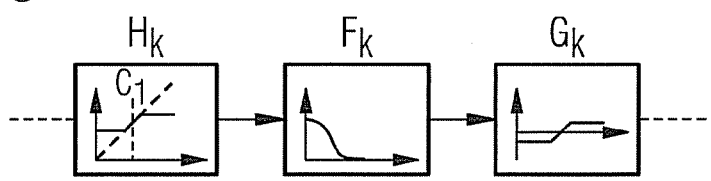

A further possibility of modifying the method according to FIG. 6A or 6B is to insert a non-linear transmission function $H_k$ which is connected upstream of the band filter $F_k$ into the branch. This is shown in FIG. 6C, with only one of several branches of the above Figures being shown in the representation in FIG. 6C. The representation of the non-linear transmission function $H_k$ is in the local domain.

This procedure is particularly meaningful in the low frequency band, in order to prevent artifacts while improving small contrast differences in the vicinity of clearly larger contrasts. The non-linear transmission function $H_1$ can be advantageously selected as $$H_1(x) = G'_1(x) + c_1 \tag{11}$$

with the parameter $c_1$ corresponding to that used in the function $G'_1$.

The dynamics of the CT values is limited by the use of $H_1$. Very large and very small values are cut off so that only a specific maximum value change is allowed compared with the CT value on the working point $c_1$.

In the example below, FIG. 8 is to show how the contrast of a native cranium scan, that is one recorded without contrast agent, can be improved. A symmetrical distortion ($G_1$: $s_1^{(u)}=1.5$, $s_1^{(d)}=1.5$, $b_1=10$, $c_1=36$) about the average value between white and grey brain matter is used. A change $G_1$ was only performed in the low frequency band, while $G_2(x)=x$ was selected in the high frequency band.

Figure 8A:
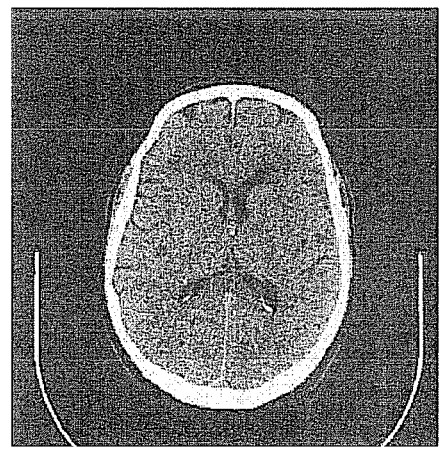
FIG. 8: shows three CT sectional images of a cranium.
Figure 8B:
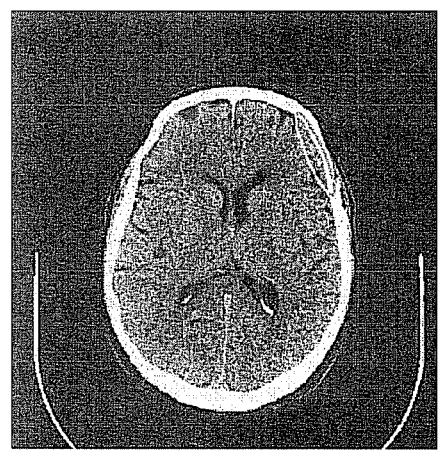
Figure 8C:
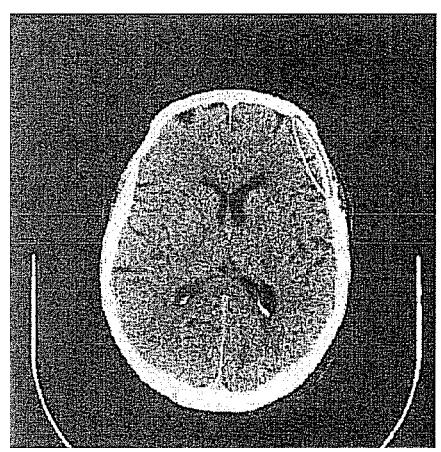

The original image can be seen in FIG. 8A. The methods according to FIGS. 6A and 6B, the result image of which is shown in FIG. 8C, cause an artificial brightening of the brain matter in the vicinity of the bone. This can be seen in FIG. 8C such that the soft tissue around the bone becomes brighter in the marked region. This problem is solved by the method as claimed in FIG. 6C ($H_1$: $s_1=1$, $b_1=15$, $c_1=36$). The result image of this method is shown in FIG. 8B: there is a clear limit between the soft tissue and the bone in the marked region. By way of this method, compared with the output image I, the contrast is raised by approximately 50% with ~6% increase in the noise. This indicates an approximately 40% better visual CNR.

In the previous representation, the functions $G_k$ are each applied uniformly to the overall image. Alternatively hereto, it is possible to use pixel-dependent parameters in the distortion functions. In this case, the function $G_k$ would not be the same for each point of an image. An adjustment to local different noise and/or the local contrast situation can be achieved as a result.

The invention was described above in an example embodiment. It is clear that numerous changes and modifications are possible without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for processing an output image of an examination object, the method comprising:
performing, by a computer processor, an image frequency division on the output image to produce a first image and a second image, the first image containing low image frequencies of the output image as a result of the image frequency division, the second image containing high image frequencies of the output image as a result of the image frequency division, the low image frequencies being less than a desired threshold frequency, the high image frequencies being greater than or equal to the desired threshold frequency;
applying a first function to the first image to modify the first image, the first function causing a contrast intensification within the first image; and
merging the modified first image and the second image to produce a resultant image, the resultant image having an increased contrast to noise ratio with respect to the output image.

2. The method as claimed in claim 1, further comprising:
applying a second function to the second image to modify the second image.

3. The method as claimed in claim 2, wherein the applying a second function reduces a noise within the second image.

4. The method as claimed in claim 3, wherein the noise reduction is limited to an image value region of the second image.

5. The method as claimed in claim 4, wherein the image value region is a function of the size of the noise of the second image.

6. The method as claimed in claim 2, wherein the applying a second function applies the second function pixel-by-pixel to the second image.

7. The method as claimed in claim 2, wherein the applying a second function causes a contrast intensification within the second image outside the image value region.

8. The method as claimed in claim 2, wherein the performing an image frequency division further produces a third image, and the method includes applying a third function to modify the third image, the second function being different from the third function.

9. The method as claimed in claim 1, further comprising:
applying a nonlinear function to the output image prior to the performing an image frequency division.

10. The method as claimed in claim 9, wherein the applying a non-linear function brings about a restriction of large image values.

11. The method as claimed in claim 1, wherein the applying a first function applies the first function such that the contrast increase is restricted to a specific image value range of the first image.

12. The method as claimed in claim 1, wherein the applying a first function applies the first function pixel-by-pixel to the first image.

13. The method as claimed in claim 1, wherein the first function is a piecemeal linear function with at least one section having a slope greater than one.

14. The method as claimed in claim 1, wherein the performing an image frequency division of the output image includes applying at least one Gaussian filter.

15. The method as claimed in claim 1, wherein the resultant image corresponds to a total of the modified first image, the second image, and the output image.

16. The method as claimed in claim 1, wherein the resultant image corresponds to a total of the modified first image and the second image, and the output image.

17. A control and computing unit for processing an output image of an examination object, the control and computing unit comprising:
a program memory configured to store program codes; and
a processor configured to, in accordance with the program codes,
perform an image frequency division on the output image to produce a first image and a second image, the first image containing low image frequencies of the output image as a result of the image frequency division, the second image containing high image frequencies of the output image as a result of the image frequency division, the low image frequencies being less than a desired threshold frequency, the high image frequencies being greater than or equal to the desired threshold frequency,
apply a first function to the first image to modify the first image, the first function causing a contrast intensification within the first image, and
merge the modified first image and the second image to produce a resultant image, the resultant image having an increased contrast to noise ratio with respect to the output image.

18. A CT-System, comprising:
the control and computing unit as claimed in claim 17; and
a CT apparatus configured to detect the output image during a relative rotational movement between a radiation source and the examination object.

19. A non-transitory computer readable medium including program segments for, when executed on a computer device, causing the computer device to:
perform an image frequency division on the output image to produce a first image and a second image, the first image containing low image frequencies of the output image as a result of the image frequency division, the second image containing high image frequencies of the output image as a result of the image frequency division, the low image frequencies being less than a desired threshold frequency, the high image frequencies being greater than or equal to the desired threshold frequency,
apply a first function to the first image to modify the first image, the first function causing a contrast intensification within the first image, and
merge the modified first image and the second image to produce a resultant image, the resultant image having an increased contrast to noise ratio with respect to the output image.

* * * * *